United States Patent [19]

Tokui et al.

[11] Patent Number: 5,270,796
[45] Date of Patent: Dec. 14, 1993

[54] APPARATUS FOR INSPECTING A PHASE SHIFT MASK

[75] Inventors: Akira Tokui; Tetsuro Hanawa, both of Itami, Japan

[73] Assignee: Mitsubishi Denki Kabushiki Kaisha, Tokyo, Japan

[21] Appl. No.: 786,768

[22] Filed: Nov. 1, 1991

[30] Foreign Application Priority Data

Nov. 13, 1990 [JP] Japan .................... 2-303789

[51] Int. Cl.$^5$ .................................. G01B 11/00
[52] U.S. Cl. ...................... 356/394; 356/398
[58] Field of Search ........... 356/237, 239, 394, 392, 356/398, 430, 431; 250/562, 572; 358/101, 106, 107

[56] References Cited

U.S. PATENT DOCUMENTS

| 4,559,603 | 12/1985 | Yoshikawa | 356/394 |
| 4,623,256 | 11/1986 | Ikenaga et al. | 356/394 |
| 4,628,531 | 12/1986 | Okamoto et al. | 356/394 |
| 4,679,938 | 7/1987 | Flamholz | 356/237 |

FOREIGN PATENT DOCUMENTS

| 0133451 | 8/1982 | Japan | 356/394 |
| 0206665 | 9/1985 | Japan. | |
| 0181805 | 8/1991 | Japan | 356/381 |

OTHER PUBLICATIONS

Electronic News, "phase-shift Masks", The Technology that is changing the lithography landscape, Peter Dunn, May 1991, pp. 28-29.

Primary Examiner—Richard A. Rosenberg
Assistant Examiner—Hoa Q. Pham
Attorney, Agent, or Firm—Leydig, Voit & Mayer

[57] ABSTRACT

An apparatus for inspecting a phase shift mask includes a light source for irradiating a pattern of a phase shift mask including a light shield member and a phase member, a phase difference detector for generating from light transmitted through the phase shift mask a phase signal including the phase difference created by the phase member, a reference signal generator for generating a reference signal, and a calculation section for detecting a defect in the phase member of the phase shift mask by comparing the phase signal with the reference signal. The reference signal may be generated from a reference mask having the same pattern as that of the phase shift pattern or from CAD data for the formation of the pattern of the phase shift mask.

9 Claims, 8 Drawing Sheets

APPARATUS FOR INSPECTING A PHASE SHIFT MASK

BACKGROUND OF THE INVENTION

1. Field of the Invention

This invention relates to a phase shift mask inspection apparatus and, more particularly, to an apparatus for detecting defects of a phase shift mask used for circuit pattern transfer.

2. Description of the Related Art

FIG. 6 shows the structure of a conventional photomask which has a transparent mask base 1 and metal layers 2 formed into desired patterns. When this photomask is uniformly irradiated with light, the light passes through the mask portions which include no metal layer 2 and which consist of mask base 1 portions alone but the light cannot pass through the other mask portions including the metal layers 2 disposed on the mask base 1. The light passing through the photomask therefore has an intensity distribution such as that shown in FIG. 7.

FIG. 8 schematically shows a conventional inspection apparatus for detecting defects in this kind of photomask. A photomask 3 on which a pair of identical patterns are formed is placed on an X-Y stage 4 which has a certain transparency. Inspection light is incident from the backside of the X-Y stage 4, travels through the stage, and irradiates the photomask 3. A pair of photodetectors 5a and 5b are disposed above the photomask 3 in correspondence with the pair of identical patterns and are connected to an inspection processing section 6.

The light which has passed through the respective patterns of the photomask 3 is detected by the photodetectors 5a and 5b, respectively, and their images are processed in the inspection processing section 6, thereby comparing and examining these two patterns. The X-Y stage 4 is moved on an X-Y plane by a stage position control section 7 to effect pattern comparison inspection over the whole surface of the photomask 3.

Since the patterns of the conventional photomask 3 is directly converted into intensities of transmitted light, the optical images received by the photodetectors 5a and 5b are processed so that a defect in one of the patterns of the photomask 3 can be discriminated by using a differential signal from these images. For example, if a metal layer defect 13c occurs in one of the two patterns 13a and 13b on the photomask 3 as shown in FIG. 9, optical images received from the photomask portion along the line A—A of FIG. 9 by the two photodetectors 5a and 5b are as shown in FIG. 10A and FIG. 10B, respectively. That is, in the optical image shown in FIG. 10B, the light intensity distribution is changed due to the metal layer defect 13c. A differential component of these optical images is extracted by the inspection processing section 6 to obtain a differential signal having a higher intensity corresponding to the defect portion as shown in FIG. 10C, thereby discriminating the pattern defect.

The conventional photomask shown in FIG. 6 is thus inspected. Recently, with the increase in transfer pattern density, use of a phase shift mask has been proposed. If the patterns become finer, bending of light into a shadow zone by the diffraction increases and resolution is reduced. A phase shift mask is used to reduce the influence of light bending into the shadow zone.

This kind of phase shift mask has, as shown in FIG. 11, a transparent mask base 21, metal layers 22 provided on the mask base 21 and formed into desired patterns, and phase members 23 formed on the mask base 21 filling appropriate spacings between adjacent metal layers 22. Each phase member 23 is formed of a glass having the same transmittance as the mask base 21 and a thickness such that a phase difference of a half wavelength occurs between the light transmitted through the base 21 and the phase member 23 and the irradiation light transmitted through the base 21 but not transmitted through the phase member 23. Light L1 passing through a surface of the mask where no phase member 23 exists and bending into the adjacent portion covered with the metallic layer 22 and light L2 passing through the phase member 23 and bending into the same portion covered with the metallic layer 22 therefore cancel each other, thereby improving the fine pattern transfer resolution.

In this type of phase shift mask, however, since the phase member 23 has the same transmittance as the mask base 21, a defect in the phase member 23 cannot appear as a change in the optical images obtained by the photodetectors 5a and 5b of the inspection apparatus shown in FIG. 8. That is, a defect in the phase member 23 of the phase shift mask cannot be discriminated by the conventional inspection apparatus shown in FIG. 8.

SUMMARY OF THE INVENTION

In view of this problem, an object of the present invention is to provide a phase shift mask inspection apparatus capable of discriminating a defect in a phase member provided on the phase shift mask.

In order to achieve this object, according to the present invention, there is provided a phase shift mask inspection apparatus comprising illumination means for irradiating a phase shift mask including a light shield member and a phase member; phase difference detection means for generating, from light transmitted through the phase shift mask, a phase signal corresponding to a phase difference created by the phase member; reference signal generation means for generating a reference signal; and calculation means for detecting a defect in the phase member of the phase shift mask by comparing the phase signal with the reference signal.

DESCRIPTION OF THE PREFERRED EMBODIMENTS

Embodiments of the present invention will be described below with reference to the accompanying drawings.

Figure 1:
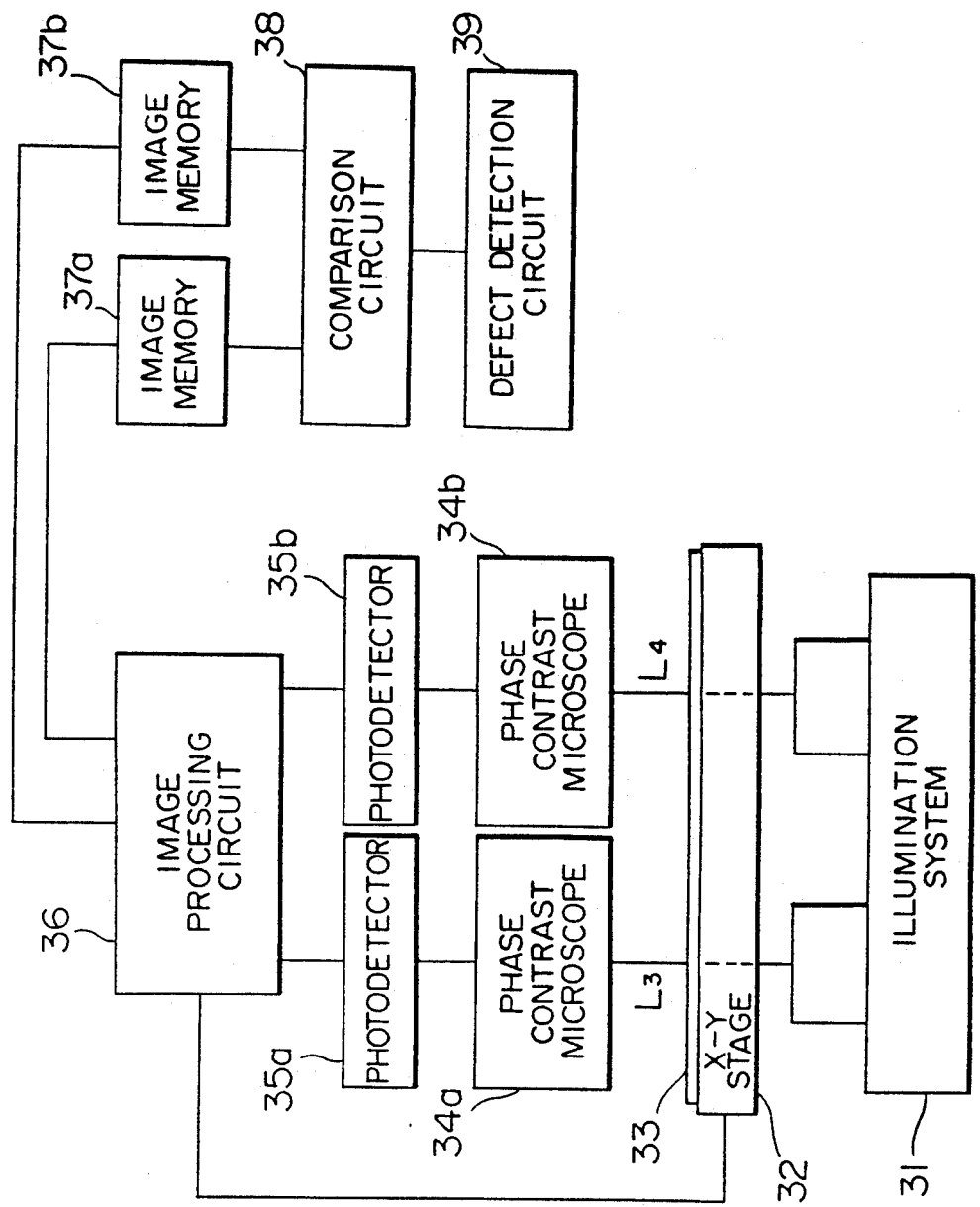
FIG. 1 is a block diagram of a phase shift mask inspection apparatus in accordance with a first embodiment of the present invention.
Figure 11:
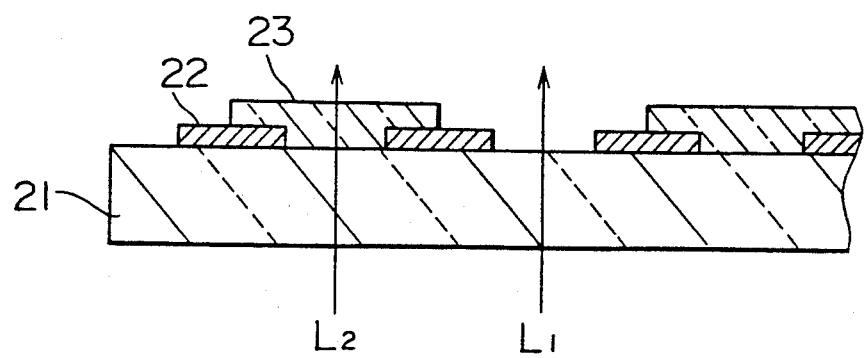
FIG. 11 is a cross-sectional view of a phase shift mask.

Referring to FIG. 1, an X-Y stage 32 is disposed opposite an illumination system 31 for emitting two inspection light beams L3 and L4 having a wavelength λ. The X-Y stage 32 has a certain transparency. A phase shift mask 33 to be inspected is placed on the X-Y stage 32. The phase shift mask 33 has a structure such as that shown in FIG. 11, that is, has light shield members consisting of metal layers formed into desired patterns on a transparent base (mask base), and phase members formed on the mask base filling appropriate spacings between adjacent light shield members. A pair of identical patterns are formed on the phase shift mask 33 though not illustrated. The two patterns of the phase shift mask 33 are respectively irradiated with the two inspection light beams L3 and L4 from the illumination system 31.

Phase contrast microscopes 34a and 34b are disposed above the X-Y stage 32 in positions such as to receive the inspection light beams L3 and L4 traveling from the illumination system 31 through the phase shift mask 33. Photodetectors 35a and 35b are respectively disposed opposite the phase contrast microscopes 34a and 34b. Outputs from the photodetectors 35a and 35b are supplied to image memories 37a and 37b through an image processing circuit 36. A comparison circuit 38 is connected to the image memories 37a and 37b, and a defect detection circuit 39 is connected to the comparison circuit 38.

The operation of this embodiment will now be described below. First, inspection light beams L3 and L4 of the wavelength λ emitted from the illumination system 31 travel through the X-Y stage 32 to irradiate the phase shift mask 33 and respectively pass through two patterns formed on the phase shift mask 33. At this time, the inspection light beams L3 and L4 passing through the phase members provided on the phase shift mask 33 are changed in phase by the phase members. The inspection light beams L3 and L4 transmitted through the phase shift mask 33 are incident upon the phase contrast microscopes 34a and 34b where the phase difference between the inspection light beams L3 and L4 is converted into light intensities. The light intensities into which the phase difference of the inspection light beams L3 and L4 have been converted are detected by the photodetectors 35a and 35b and are supplied to the image processing circuit 36.

The image processing circuit 36 collects phase difference information from the inspection light beams L3 and L4 transmitted through the phase shift mask 33 with respect to the whole of the patterns by moving the X-Y stage 32, and processes the images based on this data. The image processing circuit 36 stores, as an examined signal, the image of the inspection light beams L3 representing one of the two patterns in the image memory 37a and stores, as a reference signal, the image of the inspection light beam L4 representing the other pattern in the image memory 37b. Since these images are based on the phase difference of the inspection light beams L3 and L4, they enable determination as to whether or not the phase members of the two patterns create the desired phase difference.

Thereafter, in the comparison circuit 38, the image stored in the image memory 37a is compared with the image stored in the image memory 37b, and a defect in the phase members of the phase shift mask 33 is detected by the defect detection circuit 39.

Figure 2:
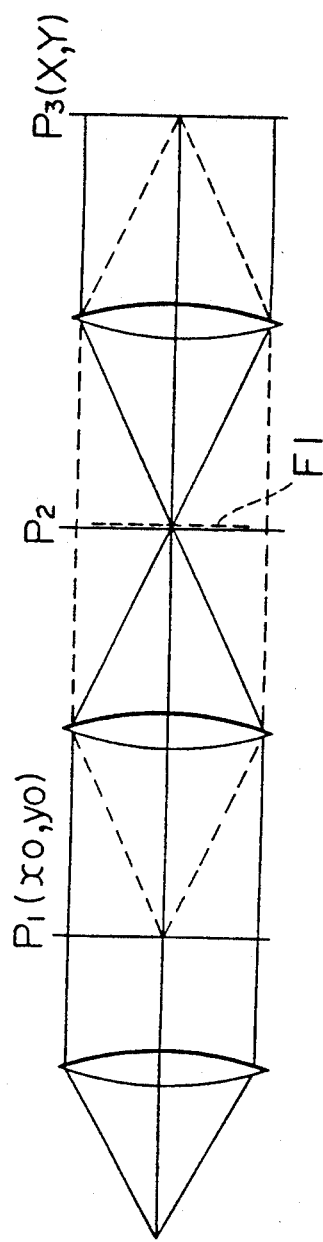
FIG. 2 is an optical path diagram relating to the principle of a phase contrast microscope.

The principle of the phase contrast microscope will be described below briefly. Ordinarily, light can be separated into an amplitude component and a phase component. A function $o_a(x_O, y_O)$ of transmission of the phase member can be expressed as $$o_a(x_O, y_O) = exp\{i\phi(x_O, y_O)\}$$

where $x_O$ and $y_O$ represent coordinates in a physical space, and $\phi(x_O, y_O)$ represents a phase difference at the position $(x_O, y_O)$. A double diffraction system such as that shown in FIG. 2 is used as the optical system, and the phase member is placed on the input plane $P_1$ of the double diffraction system. If the phase difference $\phi(x_O, y_O)$ is very small, a Fourier spectrum $O_a(N_x, N_y)$ is $$O_a(N_x, N_y) = \int\int_{-\infty}^{\infty} \{1 + i\phi(x_0, y_0)\}$$
$$exp\{2\pi i(x_0 N_x + y_0 N_y)\}dx_0 dy_0$$
$$= \delta(N_x, N_y) + i\int\int_{-\infty}^{\infty} \phi(x_0, y_0)$$
$$exp\{2\pi i(x_0 N_x + y_0 N_y)\}dx_0 dy_0.$$

This spectrum appears on the plane $P_2$ of FIG. 2. At the plane $P_2$, a direct-current component of $N_x = N_y = 0$ is cut off by a spatial filter FI, so that an output image $i_a(X, Y)$ at the output plane $P_3$ is inverse-Fourier-transformed into $$i_a(X, Y) = i\phi(X, Y).$$

X and Y represent the coordinates in the image space. Consequently, the intensity $i(X, Y)$ is $$i(X, Y) = |i_a(X, Y)|^2 = \phi^2(X, Y)$$

and the phase difference of the phase member is proportional to the square of the intensity of the image.

In the above-described embodiment, the phase shift mask 33 has two identical patterns one of which is used as a sample to be inspected while the other is used as a reference pattern. However, defects can also be detected in the same manner even if the phase shift mask 33 has three or more identical patterns.

Figure 3:
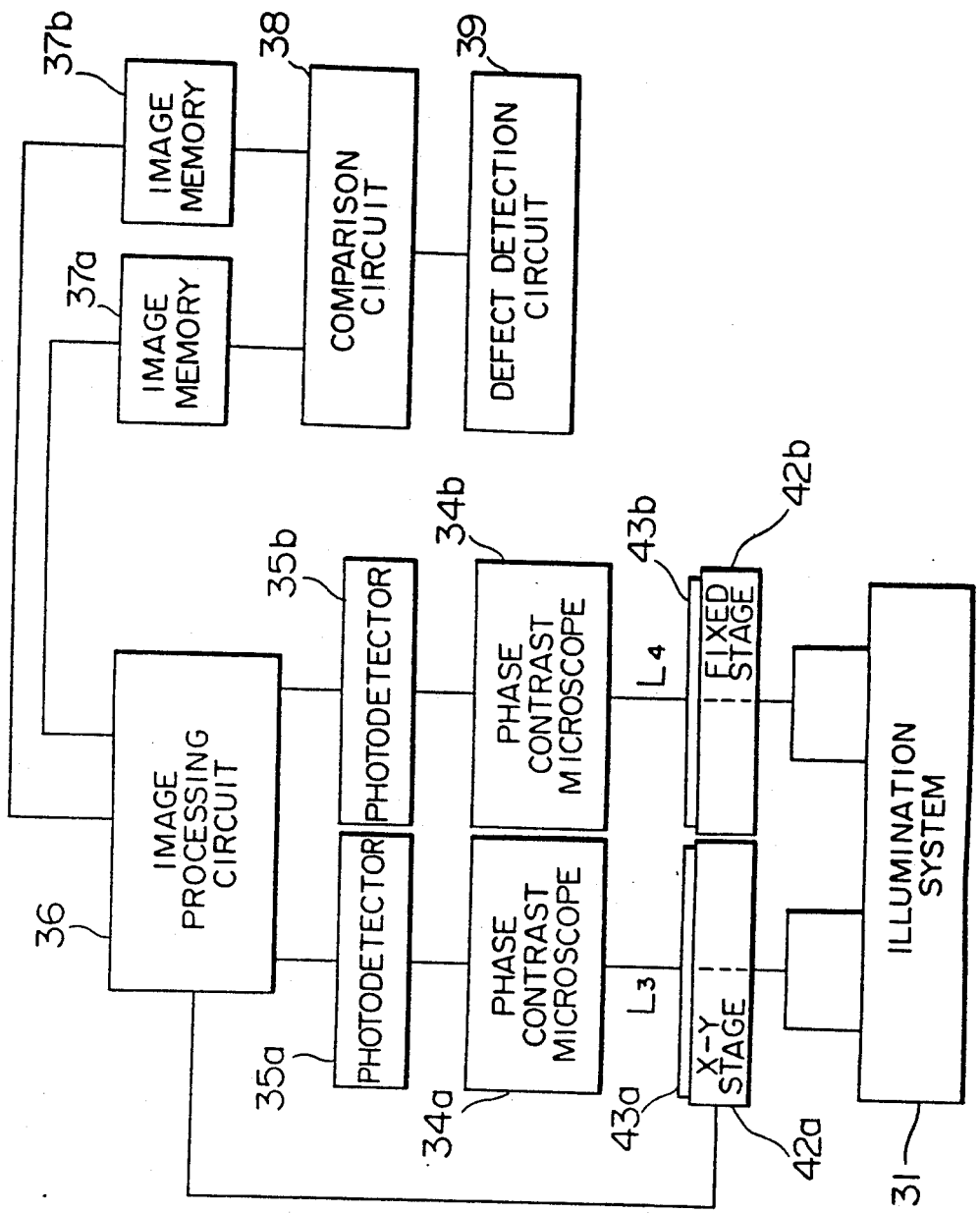
FIG. 3 is a block diagram of a second embodiment of the present invention.

FIG. 3 shows a second embodiment of the present invention in which a phase shift mask 43a which is an object to be inspected is placed on an X-Y stage 42a while a reference mask 43b is placed on a fixed stage 42b. A plurality of identical patterns are formed on the phase shift mask 43a, and reference patterns identical to the patterns formed on the phase shift mask 43a are formed on the reference mask 43b with high accuracy. The inspection light beam L3 emitted from the illumination system 31 irradiates the phase shift mask 43a through the X-Y stage 42a while the inspection light beam L4 irradiates the reference mask 43b through the fixed stage 42b. That is, the image of the patterns of the phase shift mask 43a is stored in the image memory 37a while the image of the patterns of the reference mask 43b is stored in the image memory 37b, and these images are compared with each other by the comparison circuit 38.

Figure 4:
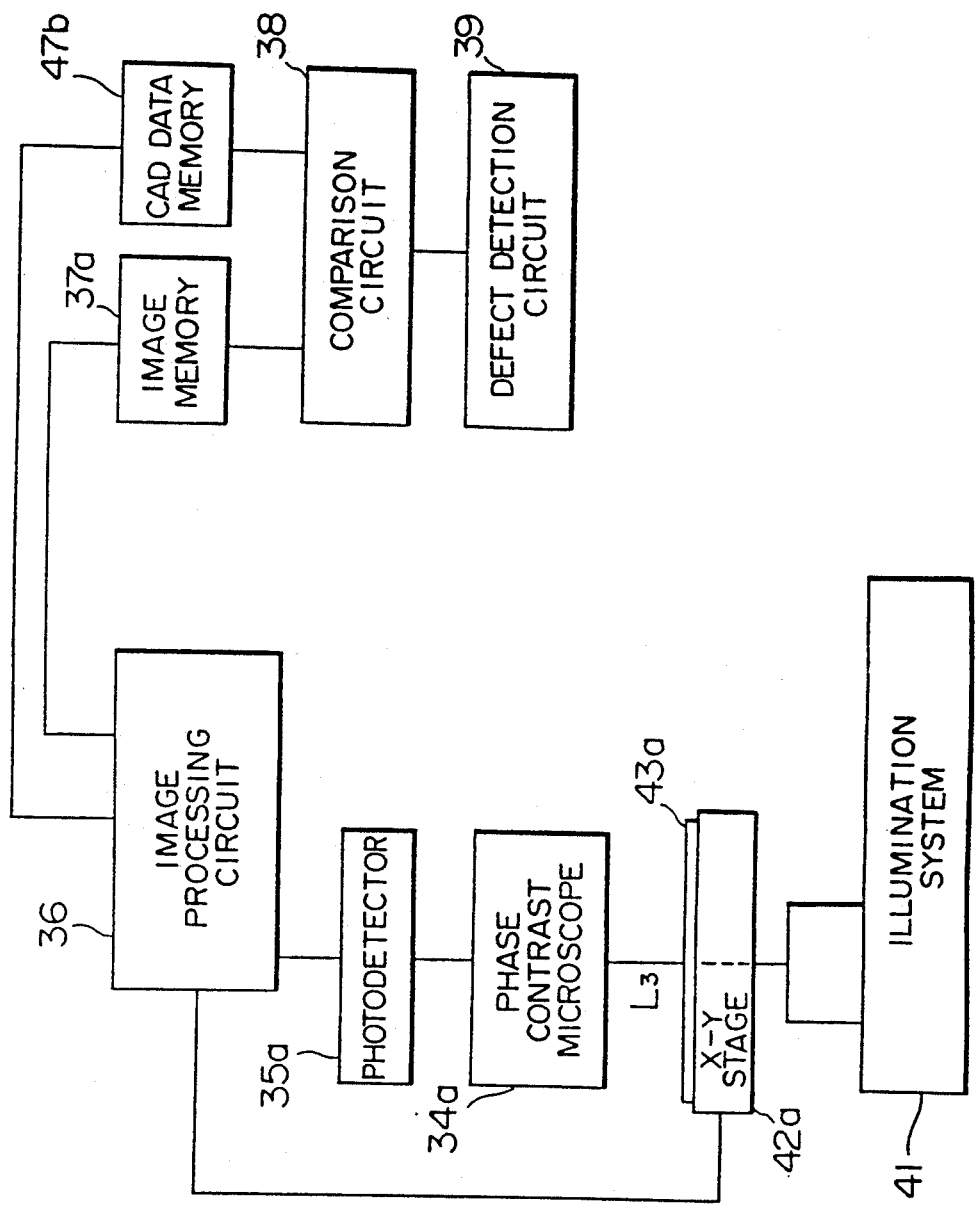
FIG. 4 is a block diagram of a third embodiment of the present invention.

FIG. 4 shows a third embodiment of the present invention which is arranged in such a manner that a CAD data memory 47b, provided in place of the image memory 37b of the second embodiment, is connected to the comparison circuit 38. CAD data on the formation of the patterns on the phase shift mask 43a is stored as a reference signal in the CAD data memory 47b. There is therefore no need for the stationary stage 42b, the reference mask 43b, the phase difference microscope 34b and the photodetector 35b used to extract the reference signal in the second embodiment. An illumination system 41 may emit only one inspection light beam L3 for irradiating the phase shift mask 43a which is an object to be inspected. The patterns of the phase shift mask 43a stored in the image memory 37a by the image processing circuit 36 is compared with the CAD data stored in the CAD data memory 47b, thereby detecting a defect in the phase shift member.

Figure 5:
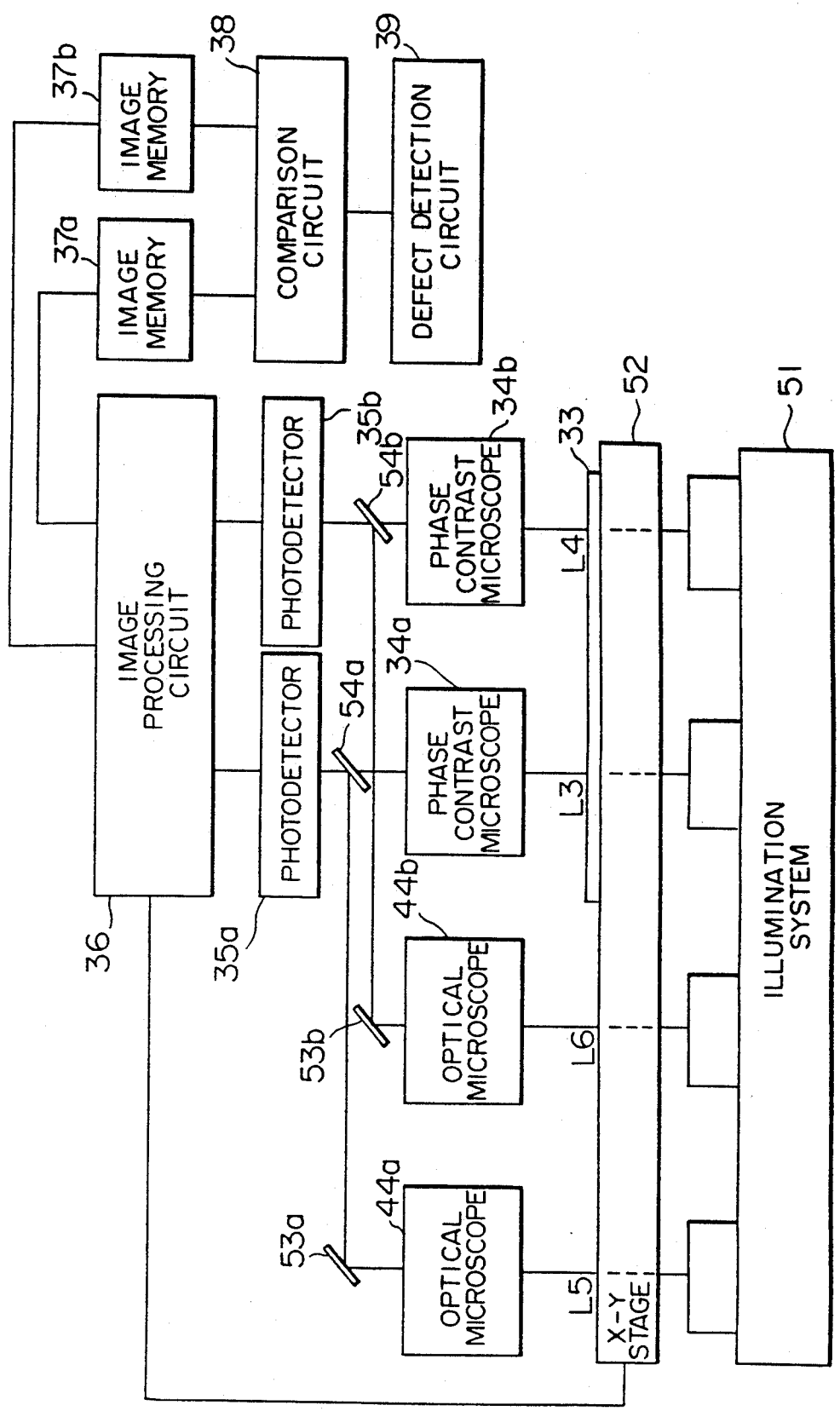
FIG. 5 is a block diagram of a fourth embodiment of the present invention.
Figure 6:
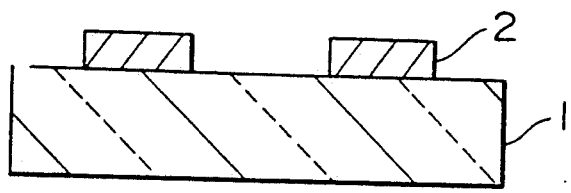
FIG. 6 is a cross-sectional view of a conventional photomask.
Figure 7:
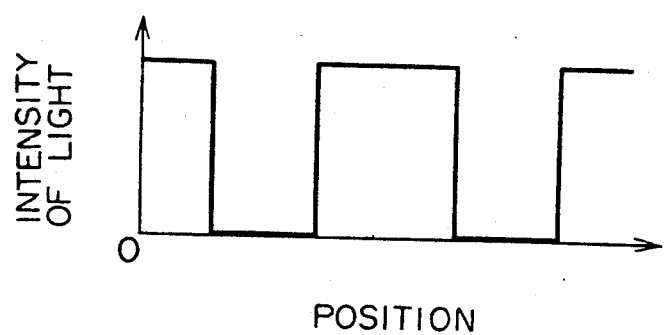
FIG. 7 is a diagram of an intensity distribution of an optical image produced by the photomask shown in FIG. 6.
Figure 8:
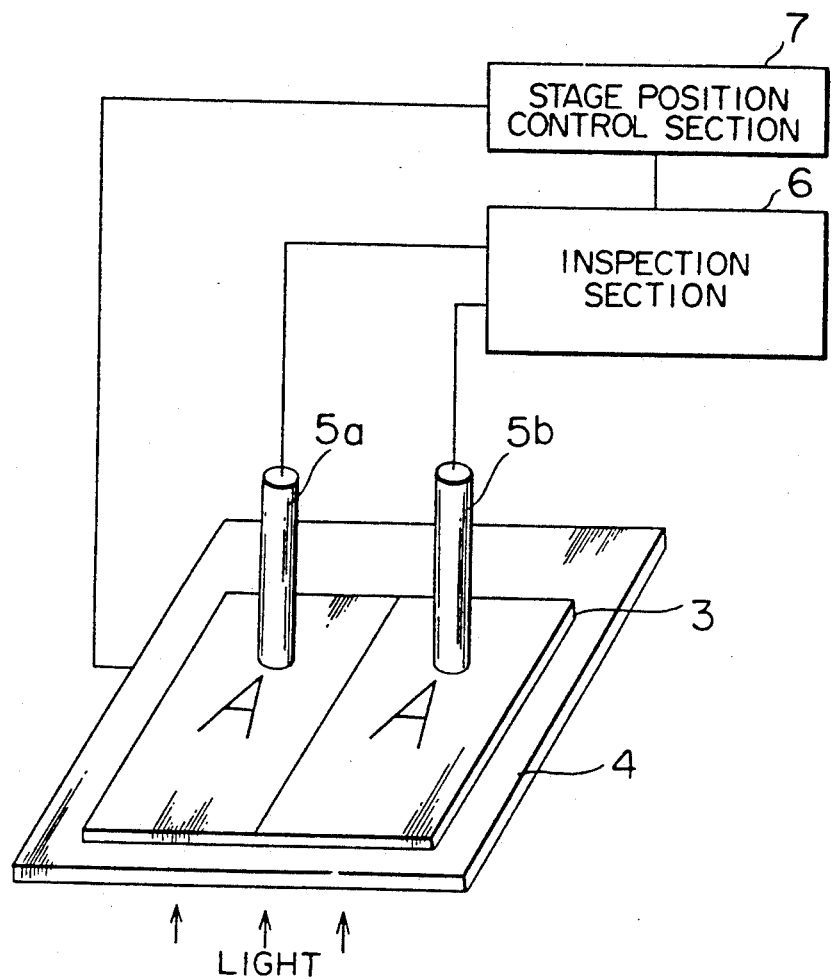
FIG. 8 is a schematic diagram of the conventional mask inspection apparatus.
Figure 9:
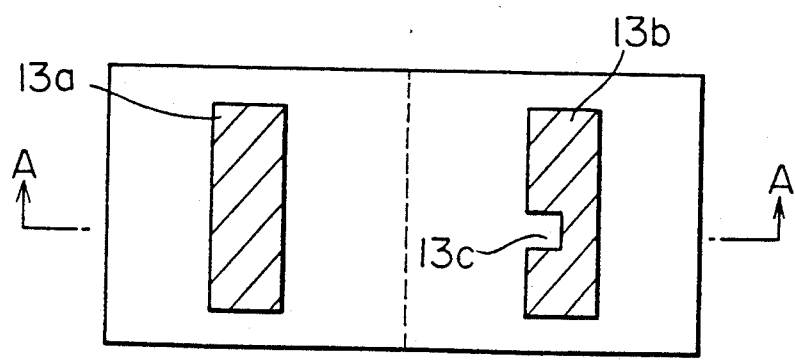
FIG. 9 is a plan view of a photomask used with the conventional apparatus.
Figure 10A:
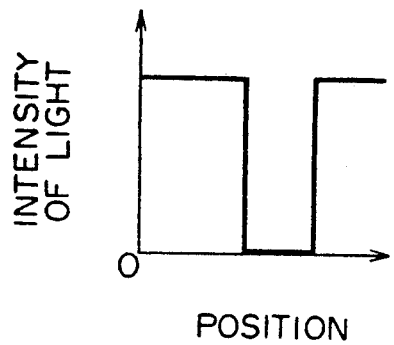
FIGS. 10A and 10B are diagrams of optical image intensity distributions produced by the photomask shown in FIG. 9.
Figure 10B:
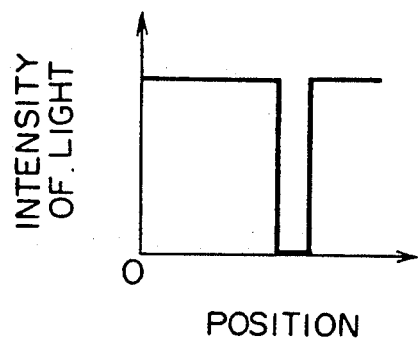
Figure 10C:
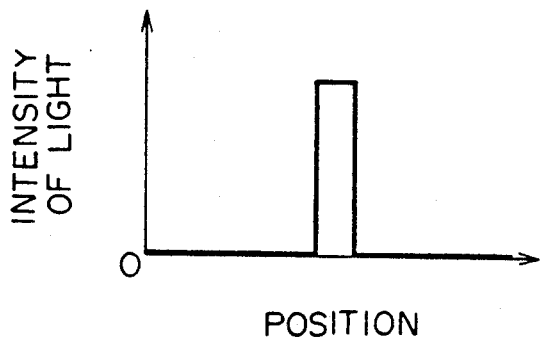
FIG. 10C is a diagram of a differential signal intensity distribution of the optical images of FIGS. 10A and 10B.

FIG. 5 shows an inspection apparatus in accordance with a fourth embodiment of the present invention. This inspection apparatus has a pair of ordinary optical microscopes 44a and 44b provided separately from the phase contrast microscopes 34a and 34b and is arranged to detect defects of the light shield member as well as defects of the phase member of the phase shift mask 33. An illumination system 51 emitting four inspection light beams L3 to L6 is used in place of the illumination system 31 of the first embodiment, and an X-Y stage which can be moved from the position below the phase contrast microscopes 34a and 34b to the position below the optical microscopes 44a and 44b is used in place of the X-Y stage 32. Further, mirrors 53a and 53b and half silvered mirrors 54a and 54b are disposed to make the inspection light beams L5 and L6 passing through the optical microscopes 44a and 44b incident upon the photodetectors 35a and 35b.

To detect a defect of the phase member, the phase shift mask 33 is moved with the X-Y stage 52 to the position below the phase contrast microscopes 34a and 34b, and inspection is performed by using the inspection light beams L3 and L4 in the same manner as the first embodiment. To detect a defect of the light shield member, the phase shift mask 33 is moved with the X-Y stage 52 to the position below the optical microscopes 44a and 44b, and inspection is performed by using the inspection light beams L5 and L6. In this embodiment, pattern images of the light shield members of the phase shift mask 33 are stored in the image memories 37a and 37b and these images are compared with each other by the comparison circuit 38.

What is claimed is:

1. An apparatus for inspecting a phase shift mask comprising:
    first illumination means for irradiating a first pattern of a phase shift mask with light, the phase shift mask including a light shielding member and a light phase shifting member;
    first phase difference detection means for generating, in response to light transmitted by the first pattern of the phase shift mask, a phase signal including the phase difference produced by the light phase shifting member;
    reference signal generation means for generating a reference signal; and
    means for detecting a defect in the light phase shifting member of the phase shift mask by comparing the phase signal with the reference signal.

2. An apparatus according to claim 1 wherein said first phase difference detection means includes a first phase contrast microscope for extracting phase difference information from the light transmitted by the first pattern of the phase shift mask, and a first photodetector for converting the phase difference information into the phase signal.

3. An apparatus according to claim 2 wherein said phase shift mask includes a second pattern that is the same pattern as the first pattern, and said reference signal generation means includes second illumination means for irradiating the second pattern of the phase shift mask with light and second phase difference detection means for generating, in response to light transmitted by the second pattern of the phase shift mask, a second phase signal including the phase difference produced by the second pattern.

4. An apparatus according to claim 3 comprising third and fourth illumination means for respectively irradiating the first and second patterns of the phase shift mask with light, first and second optical microscopes for receiving light emitted from said third and fourth illumination means and transmitted through the first and second patterns of the phase shift mask, and second calculation means for detecting a defect in the light shielding member of the phase shift mask by comparing light transmitted to said first and second optical microscopes.

5. An apparatus according to claim 1 comprising a first memory for storing the phase signal and a second memory for storing the reference signal.

6. An apparatus according to claim 1 comprising an X-Y stage for supporting a phase shift mask.

7. An apparatus according to claim 1 wherein said reference signal generation means includes a reference mask having a second pattern that is the same pattern as the first pattern of the phase shift mask, second illumination means for irradiating the second pattern of the reference mask with light, and second phase difference detection means for generating, in response to light transmitted by the second pattern of the reference mask, a second phase signal including the phase difference produced by the second pattern.

8. An apparatus according to claim 7 comprising a fixed stage for supporting the reference mask.

9. An apparatus according to claim 1 wherein said reference signal generation means includes a CAD data memory for storing CAD data for the formation of the first pattern of the phase shift mask.

* * * * *